US010005801B2

(12) United States Patent
Xian et al.

(10) Patent No.: US 10,005,801 B2
(45) Date of Patent: Jun. 26, 2018

(54) COMPOUNDS FOR PH-CONTROLLED RELEASE OF HYDROGEN SULFIDE

(71) Applicants: Washington State University, Pullman, WA (US); The Board of Supervisors of Louisiana State University and Agricultural and Mechanical College, Baton Rouge, LA (US)

(72) Inventors: Ming Xian, Pullman, WA (US); Jianming Kang, Pullman, WA (US); David J. Lefer, Saint Bernard, LA (US)

(73) Assignees: Washington State University, Pullman, WA (US); The Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days. days.

(21) Appl. No.: 15/447,797

(22) Filed: Mar. 2, 2017

(65) Prior Publication Data

US 2017/0253622 A1    Sep. 7, 2017

Related U.S. Application Data

(60) Provisional application No. 62/302,390, filed on Mar. 2, 2016.

(51) Int. Cl.
*C07F 9/44* (2006.01)
*C07F 9/572* (2006.01)

(52) U.S. Cl.
CPC .......... *C07F 9/4419* (2013.01); *C07F 9/5721* (2013.01)

(58) Field of Classification Search
CPC .... C07F 9/4071; C07F 9/5727; C07F 9/4419; C07F 9/5721
See application file for complete search history.

(56) References Cited

U.S. PATENT DOCUMENTS 9,096,504 B2 * 8/2015 Xian .................... A61K 31/095

OTHER PUBLICATIONS

Chen et al (1986) : STN International, HCAPLUS database (Columbus, Ohio), Accession No. 1986: 424359.*

* cited by examiner

*Primary Examiner* — Golam M Shameem
(74) *Attorney, Agent, or Firm* — Whitham, Curtis & Cook, P.C.

(57) ABSTRACT

The embodiments herein generally relates to compounds and methods for releasing $H_2S$ in a pH dependent manner. In particular, the invention provides compounds of various formulations which release $H_2S$ in a controlled, predictable and sustained manner upon contact with an aqueous environment, such as the circulatory system of an animal, and which are thus suitable for in vivo delivery of $H_2S$.

2 Claims, 9 Drawing Sheets

COMPOUNDS FOR PH-CONTROLLED RELEASE OF HYDROGEN SULFIDE

CROSS-REFERENCE TO RELATED APPLICATION(S)

The present application claims under 35 U.S.C. § 119, the priority benefit of U.S. Provisional Application No. 62/302,390 filed Mar. 3, 2016. The disclosure of the foregoing application is incorporated herein by reference in its entirety.

FEDERAL FUNDING ACKNOWLEDGEMENT

This invention was made with government support under Grant/Contract No R01HL116571 awarded by the National Institute of Health. The government has certain rights in the invention.

BACKGROUND OF THE INVENTION

Field of the Invention

The embodiments herein generally relate to compounds and methods for releasing $H_2S$ in a pH dependent manner. In particular, the invention provides compounds of various formulations which release $H_2S$ in a controlled, predictable and sustained manner upon contact with an aqueous environment, such as the circulatory system of an animal, and which are thus suitable for in vivo delivery of $H_2S$.

Discussion of the Related Art

Hydrogen sulfide ($H_2S$) has been recently recognized as a member of the gasotransmitter family, along with nitric oxide (NO) and carbon monoxide (CO). Studies have demonstrated that the production of endogenous $H_2S$ and the exogenous administration of $H_2S$ can exert a plurality of protective effects in many pathologies. $H_2S$ has also been shown to relax vascular smooth muscle, induce vasodilation of isolated blood vessels, and reduce blood pressure. $H_2S$ can also inhibit leukocyte adherence in mesenteric microcirculation during vascular inflammation that further suggests $H_2S$ as a potent anti-inflammatory molecule. These results as a whole strongly suggest that modulation of $H_2S$ levels has a clear therapeutic value.

Chemical tools that allow precise delivery of $H_2S$ are critical for the advancement of research in the field. Traditionally, chemical tools include, sodium sulfide ($Na_2S$) and sodium hydrogen sulfide (NaHS). These salts have the advantage of boosting $H_2S$ concentrations rapidly. However, they release $H_2S$ spontaneously in aqueous solution, making it hard to control the precise $H_2S$ concentration. In addition, $H_2S$ concentrations in aqueous solution can rapidly decrease due to volatilization, thus significantly limiting the use of these two $H_2S$ sources. As such, there is a need for the development of chemical compounds capable of controllably releasing $H_2S$ for use within biological systems.

SUMMARY OF THE INVENTION

Herein are disclosed novel compounds and associated methods for the controlled release of $H_2S$, such as in vivo as a therapeutic option or alternative or in vitro as a research tool or for other research related purposes.

Once an exemplary novel compound is exposed to an optimal pH condition, it undergoes an intramolecular cyclization that results in the production of products, which include $H_2S$, and thus allows for the delivery of $H_2S$ at a predictable and steady rate to the surrounding medium. Several types of $H_2S$ donors have been reported previously in the art and the general mechanism of action for $H_2S$ releases are controlled by different mechanisms such as hydrolysis, cellular thiol activation, and photolysis. The disclosed compounds by comparison overcome the limitation of the prior art such as GYY4137 and others of the like, via introducing structural modification to improve $H_2S$ release in the location of interest, such as the circulatory system of a subject and successfully function as to mimic natural, biological delivery of $H_2S$.

Accordingly, a first aspect of the present embodiments herein include a compound having the formula:

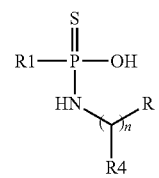

wherein R is an independent hydrogen or alkyl, substituted alkyl, aryl, aralkyl, and substituted aryl or a combination thereof; R1 is aryl, alkyl, aralkyl, and substituted aryl or a combination thereof; R4 is independently at each position a hydrogen, alkyl or a carboxylic acid wherein at least one R4 is an alkyl or carboxylic acid; n ranges from 1-6; and including a pharmaceutically acceptable salt thereof, a tautomer thereof, or a pharmaceutically acceptable salt of the tautomer.

Another aspect of the of the present embodiments herein include: a compound having the formula

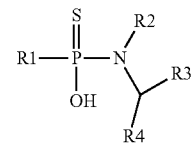

wherein R1 is aryl, alkyl, aralkyl, and substituted aryl or a combination thereof; R2 is an independent hydrogen, or a part of a heterocycle, heterocyclic, or heterocyclyl system with R3 optionally substituted, fully saturated or unsaturated, aromatic or nonaromatic cyclic group which is a 3 to 7 membered ring system; R4 is an alkyl or a carboxylic acid; and including a pharmaceutically acceptable salt thereof, a tautomer thereof, or a pharmaceutically acceptable salt of the tautomer.

Still another aspect of the embodiments herein include a method of treating a patient that would benefit from controlled $H_2S$ administration comprising the step of administering to patient a compound having the formula

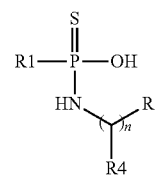

wherein R is an independent hydrogen or alkyl, substituted alkyl, aryl, aralkyl, and substituted aryl or a combination thereof; R1 is aryl, alkyl, aralkyl, and substituted aryl or a combination thereof; R4 is independently at each position a hydrogen, alkyl or a carboxylic acid wherein at least one R4 is an alkyl or carboxylic acid; n ranges from 1-6; and including a pharmaceutically acceptable salt thereof, a tautomer thereof, or a pharmaceutically acceptable salt of the tautomer.

Yet another aspect of the invention involves administering to a patient that would benefit from controlled $H_2S$ delivery a compound having the formula

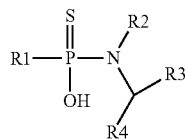

wherein R1 is aryl, alkyl, aralkyl, and substituted aryl or a combination thereof; R2 is an independent hydrogen, or a part of a heterocycle, heterocyclic, or heterocyclyl system with R3 optionally substituted, fully saturated or unsaturated, aromatic or nonaromatic cyclic group which is a 3 to 7 membered ring system; R4 is an alkyl or a carboxylic acid; and including a pharmaceutically acceptable salt thereof, a tautomer thereof, or a pharmaceutically acceptable salt of the tautomer.

As such, the compounds, as disclosed herein, are used to treat diseases or conditions that can be cured or ameliorated by the delivery of $H_2S$ and/or by an increase in the concentration of $H_2S$ at a location or environment of interest. The disclosed compounds may also be used for research purposes. Industrial and/or manufacturing uses are also within the scope of the invention.

DETAILED DESCRIPTION

Figure 1A:
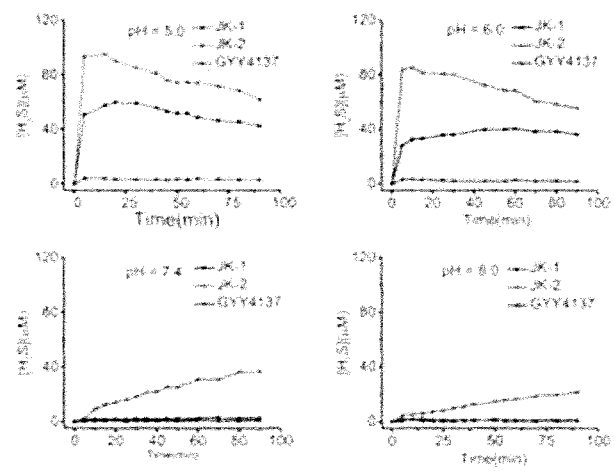
FIG. 1A. Shows $H_2S$ release profiles of JK-1, JK-2, and GYY4137 (100 μM) under different pH.

The embodiments herein provide chemical compounds that allow for the delivery of $H_2S$ to a desired environment of interest, such as the circulatory system of a subject, or to other systems wherein the measured release of $H_2S$ is desirable.

In one exemplary embodiment, as also briefly discussed above, the compounds of the invention are of the general formula 1 as seen below:

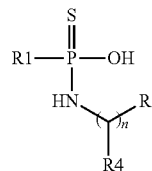

wherein R is an independent hydrogen or alkyl, substituted alkyl, aryl, aralkyl, and substituted aryl or any combination thereof. R1 is aryl, alkyl, aralkyl, and substituted aryl or any combination thereof. R4 is independently at each location an alkyl or a carboxylic acid, and n can range from 1-6 repeating units. Embodiments also include a pharmaceutically acceptable salts thereof, a tautomer thereof, or a pharmaceutically acceptable salts of the tautomer.

As another example embodiment, as also discussed briefly above, the compound of the invention can also be of the general formula 2 as seen below:

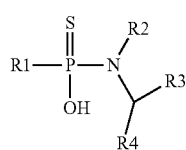

wherein R1 is aryl, alkyl, aralkyl, and substituted aryl or any combination thereof. R2 is an independent hydrogen, or can be a part of a heterocycle, heterocyclic, or heterocyclyl system with R3 optionally substituted, fully saturated or unsaturated, aromatic or nonaromatic cyclic group which is a 3 to 7 membered ring system. R4 is an alkyl or a carboxylic acid. Compounds within this embodiment also include a pharmaceutically acceptable salt thereof, a tautomer thereof, or a pharmaceutically acceptable salt of the tautomer.

Without being bound by theory, it appears that compounds of both formula 1 and 2 may generally act to release hydrogen sulfide in accordance with scheme 1 below:

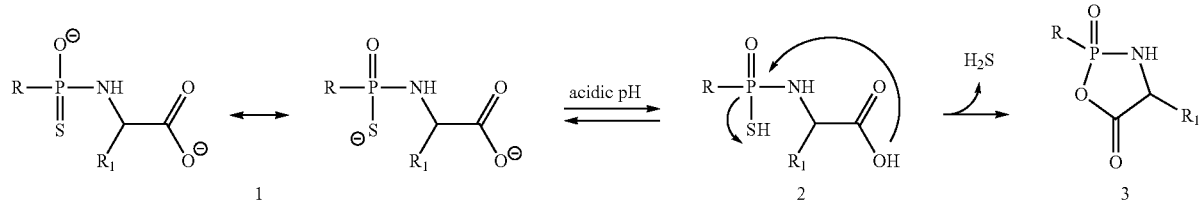

Hydrogen sulfide release from the compounds follows the process, whereby the protonation of phosphonamidothioates 1 (under neutral or slightly acidic pH) should form the corresponding phosphorothiol 2. This process facilitates the release of $H_2S$ if a nucleophilic carboxylate is presented at a suitable position. The formation of the five-membered ring product 3 is the driving force for $H_2S$ release. Such donors have unique biological applications. For example, it has been proved that $H_2S$ based therapy is promising for myocardial ischemia-reperfusion injury. Ischemic injury can lead to reduced local pH level. As such, acid-promoted $H_2S$ release would be very attractive for the treatment of ischemic injury or other injuries of the like.

Definitions

The following are definitions of terms that may be used in the present specification. The initial definition provided for a group or term herein applies to that group or term throughout the present specification individually or as part of another group, unless otherwise indicated.

The term "nucleophile", by itself means a chemical species that donates an electron-pair to an electrophile to form a chemical bond in a reaction. Because nucleophiles donate electrons, they are by definition Lewis bases. All molecules or ions with a free pair of electrons can act as nucleophiles.

"Metal" or "metal ion" includes a soluble form of a transition metal or f-block metal in an oxidation state that is known in the art.

The term "alkyl" refers to straight or branched chain unsubstituted hydrocarbon groups of 1 to 20 carbon atoms, preferably 1 to 7 carbon atoms.

The term "substituted alkyl" refers to an alkyl group substituted by, for example, one to four substituents, such as, halo, alkanoyl, aryloxy, alkanoyloxy, amino, alkylamino, substituted alkylamino, cycloalkylamino, substituted cycloalkylamino, arylamino, substituted arylamino, aralkylamino, or substituted aralkyamino.

The term "aryl" refers to monocyclic or bicyclic aromatic hydrocarbon groups having 4 to 7 carbon atoms in the ring portion, such as phenyl, with each of which may be substituted.

The term "aralkyl" refers to an aryl or a substituted aryl group bonded directly through an alkyl group, such as benzyl or the like.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, or indazole.

The term "alkenyl" refers to straight or branched chain hydrocarbon groups of 2 to 20 carbon atoms, preferably 2 to 15 carbon atoms, and most preferably 2 to 8 carbon atoms.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups from 2 to 20 carbon atoms, and most preferably 2 to 8 carbon atoms.

The term "substituted alkynyl" refers to an alkynyl group substituted by a substituent, examples include; halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated C3 C7 carbocyclic ring.

Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, which are a 4 to 7 membered monocyclic, which has at least one heteroatom in at least one carbon atom-containing ring. Each ring of the heterocyclic group containing a heteroatom may have at least one heteroatoms. The heterocyclic group may be attached at any heteroatom or carbon atom.

The term "heteroatoms" can include oxygen, sulfur and nitrogen.

The term "ring structure" refers to an organic cyclic compound in which an organic compound containing a series of atoms is connected to form a loop or ring. The term includes various cyclic compounds, which may be: saturated, unsaturated or aromatic; substituted or unsubstituted; hetero- or homo-cyclic; and may be mono- or polycyclic, as described herein. As used herein hetero-structures are those in which not all atoms of the primary structure are carbon. Instead, one or more are a different atom, for example a 6-membered ring in which 5 of the ring atoms are C and one is N.

The terms "parenteral carrier system" (including variations thereof such as the various specific injectable and infusible dosage forms) refer to compositions comprising one or more pharmaceutically suitable excipients, such as solvents like water and co-solvents, solubilizing compounds, wetting compounds, suspending compounds, thickening compounds, emulsifying compounds, chelating compounds, buffers, pH adjusters, antioxidants, reducing compounds, antimicrobial preservatives, bulking compounds, protectants, tonicity adjusters, and special additives.

The terms "therapeutically effective dose" (and variations thereof) refer to an amount, dose or dosing regimen of a compound (i.e., active pharmaceutical ingredient, prodrug or precursor thereof) that upon interaction with a biological material is sufficient to treat or prevent injury of a biological material exposed in hypoxic or ischemic conditions, whereby such dose may vary depending on the form of the compound, the biological material's condition and/or severity, the route of administration, the age of the biological material, and the like.

The compounds of formula 1 and 2 may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula 1 or 2 may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula 1 or 2 may form salts with a variety of organic and inorganic acids. Such salts include those formed with hydrogen chloride, hydrogen bromide, methanesulfonic acid, sulfufric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions may be formed.

All stereoisomers of the compounds of the instant invention are contemplated, either in admixture or in pure or substantially pure form. The definition of compounds according to the invention includes all the possible stereoisomers and their mixtures. Particularly preferred are the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

It should be emphasized that the above-described embodiments and following specific examples of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

General Description

Hydrogen sulfide is produced naturally in small but detectable amounts in a selected cell. Hydrogen sulfide by itself has a number of biological functions such as a critical signaling molecule that regulates many physiological and/or pathological processes.

Similar to nitric oxide, hydrogen sulfide has been shown to relax smooth muscle, and due to this property, hydrogen sulfide has also been recognized as a potentially treatment option for disease states such a cardiovascular disease. With hydrogen sulfide overcoming the limitations of nitric oxide, hydrogen sulfide will not form harmful peroxides that nitric oxides does by interacting with a superoxide in a system. The compounds of this disclosure herein, with their predictable and controllable release mechanism make them highly desirable for cardiovascular disease applications and the like.

Additional applications for the disclosed compounds also include opportunities for the therapeutic treatment of erectile dysfunction, similar to current nitric oxide compounds. Moreover, the embodiments herein can be utilized for the treatment of Alzheimer's disease, given the severely decreased concentration of hydrogen sulfide in the brain. Accordingly, such a treatment option allows for a reversal of this condition and allows for the reduction of symptoms associated with Alzheimer's.

The ability of hydrogen sulfide to affect smooth muscle thus makes the compounds of the embodiments herein useful in the treatment and/or prevention of disease states or conditions, which involve the circulatory system. The compounds of this disclosure allow for treatment options that require altered blood flow, abnormal blood pressure, and or oxygen deprivation. The release of $H_2S$ within a patient results in the relaxation of smooth muscle, and an increase circulation of blood as a whole. In some embodiments, the compounds of this disclosure are also capable of being utilized in the treatment and/or prevention of myocardial ischemia-reperfusion injury, homorragic shock or other ischemic states.

The compounds of the invention may additionally be utilized in patients that are or have undergone traumatic injury. The traumatic injury can occur from external effects such as burns, amputations, puncher wounds, surgical trauma, or cardiac arrest, heart attack or other such traumatic events that result in an acute reduction in circulation.

Conditions that may result in the acute reduction in circulation may result in or cause or be caused by one or more of the following, which can also be treated or prevented by use of the compounds disclosed herein: myocardial infarction, sepsis, vascular abnormalities, cirrhosis, liver injury, kidney injury, vascular calcification, gastric injury induced by drug treatment, burns, lung injury, neutrophil adhesion, leukocyte-mediated inflammation, erectile dysfunction, irritable bowel syndrome, anti-nociceptive effects in post-inflammatory hypersensitivity, acute coronary syndrome, cardiac arrest, planned cardiac bypass surgery, congestive heart failure, neonatal hypoxia/ischemia, myocardial ischemic reperfusion injury, unstable angina, post-angioplasty, aneurysm, trauma, stroke, hemorrhagic shock, and/or blood loss, or the like, and the compounds of the invention may be used to prevent or to treat any of these conditions. A therapeutically effective dose of the compounds of the embodiments herein invention is administered to the patient before, after, or both before and after.

The compounds of the invention can also be utilized in the treatment and/or prevention of disease states or conditions that result in hypertension. Conditions, which can be treated by the compounds herein that result in hypertension include one or more of the following: aneurysm, stroke, metabolic syndrome, liver injury, dementia, kidney injury, kidney disease, vascular calcification, angina, peripheral artery disease, transient ischemic attack, or the like, and the compounds of the invention may be used to prevent or to treat any of these conditions. A therapeutically effective dose of the compounds of the invention is administered to the patient before, after, or both before and after.

The compounds of the invention can also be utilized in tissue regeneration and general wound healing by increasing blood flow to damaged tissues that aids in tissue regeneration and wound healing. Treating the injured area with the compounds of the invention thus aids in the wound healing and tissue regeneration process by managing the biological processes that inhibit healing and regeneration such as increasing blood flow.

Other methods of using the compounds of the invention include pre-treating a patient prior to an ischemic or hypoxic injury or disease insult. Such methods are used when an injury or disease, with the potential to cause ischemia or hypoxia, is scheduled or elected in advance, or predicted in advance to likely occur.

The compounds of the invention may be formulated into various forms for various routes of administration. Administration of a therapeutically effective dose will consist of one or more of the compounds as required. Administration of the compounds of the invention, or their pharmaceutically acceptable salts, in pure form or in an appropriate pharmaceutical composition, can be carried out via any of the accepted modes of administration of compounds for serving similar utilities. The pharmaceutical compositions of the invention can be prepared by combining at least one compound of the invention with an appropriate pharmaceutically acceptable carrier, diluent or excipient, and may be formulated. Pharmaceutical compositions of the invention are formulated so as to allow the active ingredients contained therein to be bioavailable upon administration of the composition to a patient.

The compositions of the invention typically contain the compounds in an amount that is sufficient to prevent or treat the condition/disease of interest. While any suitable amount of compound may be present in a composition, the amount generally ranges from about 1-99% by weight of all ingredients.

In other embodiments, the compounds of the invention may have non-biological applications. For example, the compounds of the invention or H$_2$S produced from the compounds of the invention may be used for the synthesis of other compounds, or in other manufacturing or industrial processes.

The embodiments herein also provide methods of using the compounds described herein. Exemplary methods include but are not limited to, for example, therapeutic methods in which one or more of the compounds are administered in order to prevent or treat a condition or disease. The method(s) can involve the steps of identifying a patient or subject with the disease or condition of interest, determining a suitable dosage of the compound(s), and administering the compound(s) to the subject/patient. Further, the methods may involve monitoring the response of the patient to the drug, and/or the outcome of treatment, and the modification of the original protocol as needed.

Those of ordinary skill in the art recognize that, in some embodiments, the outcome may be a cure in that all disease symptoms disappear and do not return for at least a period of time. However, in other cases, administration may be ongoing in order to keep the condition or disease or symptoms to an acceptable level, or at least to a level that is lower than that experienced by the patient in the absence of treatment. Even a partial lessening of symptoms may be highly beneficial. In addition, the compounds of the invention may be administered in conjunction with the administration of other therapies or therapeutic compounds, e.g. other compounds suitable for treating the disease or condition which the compound is intended treat or prevent.

EXAMPLES

Synthesis

A series of donors were synthesized from phenylphosphonothioic dichloride 4. Briefly, 4 was subsequently treated with 3-hydroxypropionitrile and a C-protected amino acid to provide the precursor 5. Then LiOH-mediated hydrolysis of 5 provided the donor products in good overall yields. Five amino acids (glycine, phenylalanine, valine, alanine, and proline) were employed to prepare these donors. All of these products were fully characterized.

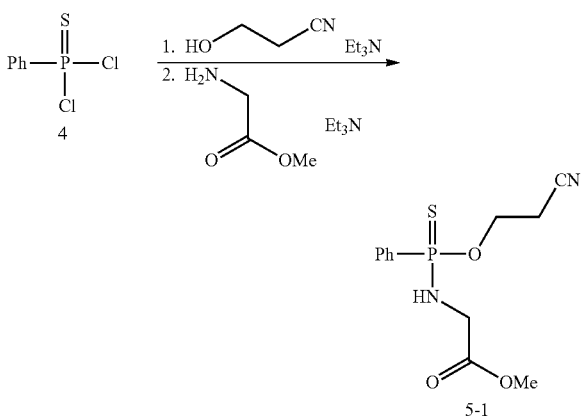

Phosphonothioic dichloride (0.45 mL, 3 mmol) was dissolved in 3.5 mL of anhydrous dichloromethane (CH$_2$Cl$_2$). To this solution was added 3-hydroxypropionitrile (0.2 mL, 3 mmol) and triethylamine (0.45 ml, 3 mmol) under an Ar$_{(g)}$ atmosphere at 0° C. The reaction was stirred at 0° C. for 15 min and at room temperature for 3 h. A solution of glycine methyl ester (0.414 g, 3.3 mmol), triethylamine (1.25 ml, 9 mmol), and 3.5 mL anhydrous dichloromethane (CH$_2$Cl$_2$) was added and the reaction was stirred for an additional 3 h. The mixture was diluted with 10 ml dichloromethane (CH$_2$Cl$_2$), washed with 10 mL of 2 M H$_2$SO$_4$, dried (MgSO$_4$), and concentrated under reduced pressure. The crude material was purified by flash chromatography to afford the precursor 5-1 as a yellow oil (554 mg, 65%). $^1$H NMR (300 MHz, CDCl$_3$) δ 7.88 (m, 2H), 7.51 (m, 3H), 4.35 (m, 2H), 3.74 (m, 2H), 3.73 (s, 3H), 3.00 (m, 1H), 2.82 (t, J=6.0 Hz, 2H); $^{13}$C NMR (75 MHz, CDCl$_3$) δ 171.50, 132.54, 131.00, 129.03, 128.83, 117.38, 59.62, 52.69, 43.47, 20.05; $^{31}$P NMR (122 MHz, CDCl$_3$) δ 78.70; FTIR (cm$^{-1}$) 3328.92, 2918.28, 2848.84, 2254.59, 1740.53, 1436.99, 1210.98, 1119.55, 1038.13, 727.58; HRMS m/z 299.0615 [M+H]$^+$; calcd for C$_{12}$H$_{16}$N$_2$O$_3$PS 299.0613.

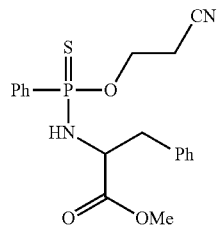

5-2

5-2 was prepared from L-phenylalanine methyl ester using the same procedure as for 5-1. 5-2 was a mixture of two inseparable diastereomers. $^1$H NMR (300 MHz, CDCl$_3$) δ 7.70 (m, 4H), 7.47 (m, 2H), 7.39 (m, 4H), 7.27 (m, 6H), 7.14 (m, 4H), 4.18 (m, 4H), 3.88 (m, 2H), 3.71 (s, 3H), 3.56 (s, 3H), 3.03 (m, 2H), 2.88 (m, 2H), 2.61 (m, 4H); $^{13}$C NMR (75 MHz, CDCl$_3$) δ 173.40, 173.26, 136.45, 136.04, 134.53, 134.02, 132.42, 132.38, 132.27, 132.23, 130.90, 130.88, 130.73, 129.78, 128.90, 128.77, 128.59, 127.41, 117.30, 117.26, 59.31, 58.98, 56.79, 56.23, 52.72, 52.51, 40.67, 40.55, 19.90, 19.79; $^{31}$P NMR (122 MHz, CDCl$_3$) δ 77.58, 77.06; FTIR (cm$^{-1}$) 3338.52, 3028.55, 2955.85, 2253.51, 1738.55, 1435.96, 1169.59, 1034.29, 904.29, 726.66; HRMS m/z 389.1080 [M+H]$^+$; calcd for C$_{19}$H$_{22}$N$_2$O$_3$PS 389.1083; yield: 71%.

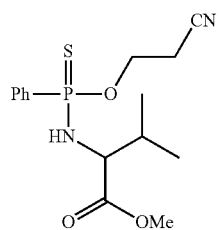

5-3

5-3 was prepared from valine methyl ester using the same procedure as for 5-1. 5-3 was a mixture of inseparable diastereomers. $^1$H NMR (300 MHz, CDCl$_3$) δ 7.87 (m, 4H), 7.46 (m, 6H), 4.32 (m, 2H), 4.22 (m, 2H), 4.10 (q, J=7.1 Hz, 1H), 3.88 (m, 1H), 3.71 (s, 3H), 3.59 (s, 3H), 3.03 (m, 2H), 2.77 (m, 4H), 2.03 (m, 2H), 0.89 (dd, J=15.0, 6.8 Hz, 6H), 0.80 (t, J=6.7 Hz, 6H); $^{13}$C NMR (75 MHz, CDCl$_3$) δ 173.48, 173.27, 134.22, 133.40, 132.79, 132.29, 132.26, 132.10, 132.07, 131.97, 131.08, 130.97, 130.71, 130.60, 128.61, 128.56, 128.46, 128.42, 116.97, 60.35, 59.91, 59.59, 59.49, 52.21, 52.02, 32.13, 32.01, 19.81, 19.73, 19.63, 19.04, 17.70, 17.36; $^{31}$P NMR (122 MHz, CDCl$_3$) δ 78.43, 77.91; FTIR (cm$^{-1}$) 3351.44, 2966.76, 2253.25, 1738.19, 1437.24, 1256.89, 1139.12, 1041.04, 928.57, 728.33; HRMS m/z 363.0907 [M+Na]$^+$; calcd for C$_{13}$H$_{17}$N$_2$NaO$_3$PS 363.0902; yield: 72%.

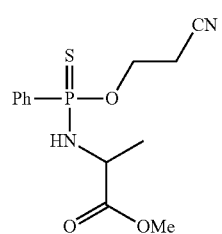

5-4

5-4 was prepared from L-alanine methyl ester using the same procedure as for 5-1. 5-4 was a mixture of two inseparable diastereomers. $^1$H NMR (300 MHz, CDCl$_3$) δ 7.98-7.75 (m, 4H), 7.61-7.34 (m, 6H), 4.40-4.17 (m, 4H), 4.08 (m, 1H), 3.92 (m, 1H), 3.71 (s, 3H), 3.68 (s, 1H), 3.65 (s, 1H), 3.64 (s, 3H), 2.86-2.72 (m, 4H), 1.38 (d, J=7.1 Hz, 4H), 1.30 (d, J=6.9 Hz, 2H); $^{13}$C NMR (75 MHz, CDCl$_3$) δ 174.39, 174.31, 132.44, 132.40, 130.95, 130.91, 130.76, 128.94, 128.85, 128.74, 117.32, 59.59, 59.53, 52.83, 52.70, 50.81, 50.63, 21.36, 21.29, 20.10, 19.99; $^{31}$P NMR (122 MHz, CDCl$_3$) δ 77.57, 77.14; FTIR (cm$^{-1}$) 3313.75, 2953.27, 2254.28, 1736.19, 1437.15, 1209.47, 1142.64, 1038.70, 997.27, 727.50; HRMS m/z 335.0590 [M+Na]$^+$; calcd for C$_{13}$H$_{18}$N$_2$NaO$_3$PS 335.0589; yield: 64%.

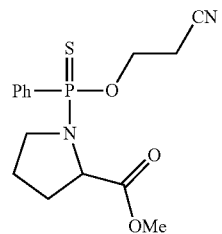

5-5

5-5 was prepared from proline methyl ester using the same procedure as for 5-1. $^1$H NMR (300 MHz, CDCl$_3$) δ 7.80 (m, 2H), 7.48 (m, 3H), 4.62 (m, 1H), 4.44 (m, 2H), 3.74 (s, 3H), 3.25 (m, 1H), 2.87 (m, 3H), 2.16 (m, 1H), 1.96 (m, 2H), 1.82 (m, 1H); $^{13}$C NMR (75 MHz, CDCl$_3$) δ 175.36, 132.00, 130.96, 130.81, 128.89, 117.56, 62.07, 59.54, 52.49, 47.31, 31.20, 26.15, 20.20; $^{31}$P NMR (122 MHz, CDCl$_3$) δ 75.65; FTIR (cm$^{-1}$) 3313.75, 2953.27, 2254.28, 1736.19, 1437.15, 1209.47, 1142.64, 1038.70, 997.27, 727.50; HRMS m/z 335.0590 [M+Na]$^+$; calcd for C$_{13}$H$_{18}$N$_2$NaO$_3$PS 335.0589; yield: 68%.

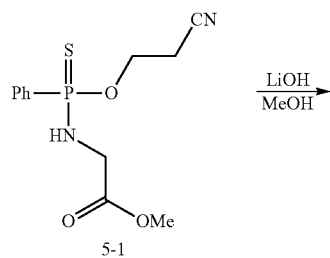

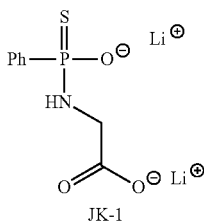

5-1 (150 mg, 0.5 mmol) was dissolved in 2 mL of methanol. To this mixture was added 2 mL of 1M LiOH aqueous solution (freshly prepared). The resultant solution was stirred at room temperature for 12 h and concentrated to dryness. The resulting solid was suspended in anhydrous methanol, filtered (0.2 μm Teflon membrane), and concentrated. The final product JK-1 was obtained as white solid in 88% yield after lyophilization. $^1$H NMR (300 MHz, DMSO-$d_6$) δ 7.72 (m, 2H), 7.21 (m, 3H), 3.24 (m, 1H), 3.04 (m, 1H), 2.88 (m, 1H); $^{13}$C NMR (75 MHz, DMSO-$d_6$) δ 176.95, 146.23, 144.57, 131.17, 128.52, 127.52, 47.37; $^{31}$P NMR (122 MHz, DMSO-$d_6$) δ 52.37; FTIR (cm$^{-1}$) 3281.49, 1583.31, 1416.59, 1317.95, 1122.45, 1086.93, 997.31, 862.57, 749.06, 713.46; HRMS m/z 250.0443 [M+Li]$^+$; calcd for $C_8H_8Li_3NO_3PS$ 250.0443.

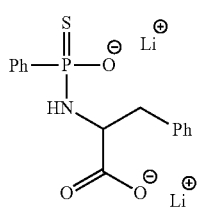

JK-2 was prepared from 5-2 using the same procedure as for JK-1. JK-2 was a mixture of two inseparable diastereomers. $^1$H NMR (300 MHz, DMSO-$d_6$) δ 7.61 (m, 4H), 7.14 (m, 14H), 6.94 (m, 2H), 4.12 (s, 2H), 3.16 (m, 2H), 3.01 (m, 2H), 2.85 (m, 2H); $^{13}$C NMR (75 MHz, DMSO-$d_6$) δ 179.40, 176.72, 147.21, 145.82, 141.22, 140.64, 131.43, 131.34, 130.54, 130.18, 128.54, 128.37, 128.04, 127.49, 127.33, 126.92, 126.01, 125.88, 59.24, 57.95, 25.96; $^{31}$P NMR (122 MHz, DMSO-$d_6$) δ 54.59, 52.15; FTIR (cm$^{-1}$) 3307.57, 1580.82, 1495.95, 1417.79, 1084.59, 950.40, 816.72, 713.43; HRMS m/z 340.0925 [M+Li]$^+$; calcd for $C_{15}H_{14}Li_3NO_3PS$ 340.0906; yield: 90%.

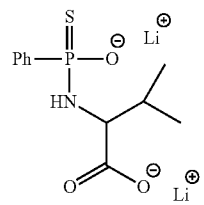

JK-3 was prepared from 5-3 using the same procedure as for JK-1. JK-3 was a mixture of two inseparable diastereomers. $^1$H NMR (300 MHz, DMSO-$d_6$) δ 7.81 (m, 4H), 7.21 (m, 6H), 3.86 (m, 1H), 3.00 (m, 2H), 2.61 (m, 1H), 2.21 (m, 1H), 1.68 (m, 1H), 0.84 (d, J=6.8 Hz, 3H), 0.64 (d, J=6.8 Hz, 3H), 0.56 (d, J=6.6 Hz, 3H), 0.44 (d, J=6.7 Hz, 3H); $^{13}$C NMR (75 MHz, DMSO-$d_6$) δ 180.08, 147.53, 145.79, 144.07, 131.95, 131.24, 131.11, 128.57, 127.44, 64.07, 61.68, 31.54, 31.42, 20.96, 20.61, 18.99, 18.35; $^{31}$P NMR (122 MHz, DMSO-$d_6$) δ 57.34, 53.16; FTIR (cm$^{-1}$) 3304.87, 2961.60, 1575.57, 1434.98, 1121.20, 1082.62, 1064.04, 890.78, 713.86; HRMS m/z 292.0923 [M+Li]$^+$; calcd for $C_{11}H_{14}Li_3NO_3PS$ 292.0906; yield: 93%.

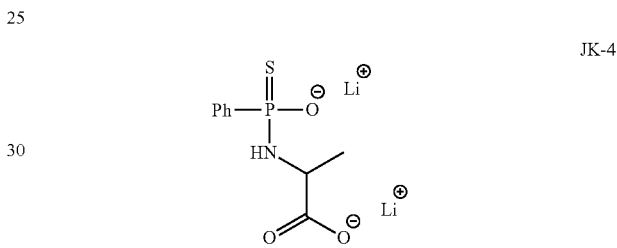

JK-4 was prepared from 5-4 using the same procedure as for JK-1. JK-4 was a mixture of two inseparable diastereomers. $^1$H NMR (300 MHz, DMSO-$d_6$) δ 7.75 (m, 4H), 7.19 (m, 6H), 3.51 (m, 2H), 3.14 (s, 1H), 3.03 (m, 1H), 1.07 (d, J=6.1, 3H), 0.87 (d, J=6.9, 3H); $^{13}$C NMR (75 MHz, DMSO-$d_6$) δ 181.03, 180.68, 146.86, 146.21, 145.16, 144.52, 131.34, 131.15, 128.63, 127.57, 52.74, 52.64, 22.76, 21.54; $^{31}$P NMR (122 MHz, DMSO-$d_6$) δ 53.00, 51.24; FTIR (cm$^{-1}$) 3268.08, 1416.88, 1122.49, 1086.58, 971.75, 860.16, 713.22; HRMS m/z 264.0604 [M+Li]$^+$; calcd for $C_9H_{10}Li_3NO_3PS$ 264.0599; yield: 91%.

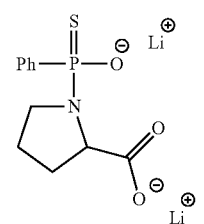

JK-5 was prepared from 5-5 using the same procedure as for JK-1. $^1$H NMR (300 MHz, DMSO-$d_6$) δ 7.86 (m, 2H), 7.23 (m, 3H), 4.02 (m, 1H), 2.64 (m, 1H), 2.01 (m, 1H), 1.58 (m, 4H); $^{13}$C NMR (75 MHz, DMSO-$d_6$) δ 180.56, 144.36, 142.67, 132.26, 129.22, 127.36, 61.93, 48.38, 30.66, 26.26; $^{31}$P NMR (122 MHz, DMSO-$d_6$) δ 62.10; FTIR (cm$^{-1}$) 3341.01, 1574.13, 1418.28, 1306.60, 1121.59, 1063.12, 927.89, 864.36, 715.69; HRMS (Maldi) m/z 290.0767 [M+Li]$^+$; calcd for $C_{11}H_{12}Li_3NO_3PS$ 290.0750; yield: 90%.

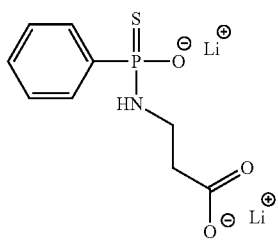

JK-6

JK-6 was prepared from 5-6 using the same procedure as for JK-1. $^1$H NMR (600 MHz, DO) δ 7.68 (m, 2H), 7.36 (m, 3H), 2.81 (m, 2H), 2.17 (t, 2H); $^{13}$C NMR (150 MHz, D$_2$O) δ 181.13, 140.41, 129.92, 129.85, 128.26, 48.81, 39.19, 38.69; $^{31}$P NMR (244 MHz, D$_2$O) δ 56.98; HRMS m/z 244.0200 [M+H−2Li]$^+$; calcd for C$_9$H$_{11}$NO$_3$PS 244.0208.

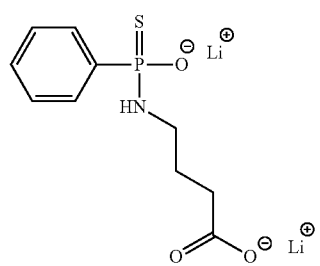

JK-7

JK-7 was prepared from 5-7 using the same procedure as for JK-1. $^1$H NMR (600 MHz, D$_2$O) δ 7.67 (m, 2H), 7.34 (m, 3H), 2.59 (m, 2H), 2.00 (t, 2H), 1.53 (m, 2H); $^{13}$C NMR (150 MHz, D$_2$O) δ 183.16, 140.42, 129.95, 129.88, 128.23, 41.46, 35.02, 27.90; $^{31}$P NMR (244 MHz, D$_2$O) δ 56.95; HRMS m/z 258.0345 [M+H−2Li]$^+$; calcd for C$_{10}$H$_{13}$NO$_3$PS 258.0365.

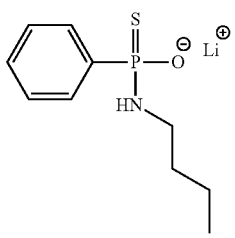

JK-8

JK-8 was prepared from 5-8 using the same procedure as for JK-1. $^1$H NMR (600 MHz, D$_2$O) δ 7.68 (m, 2H), 7.35 (m, 3H), 2.59 (m, 2H), 1.26 (m, 2H), 1.12 (m, 2H), 0.68 (t, 3H); $^{13}$C NMR (150 MHz, D$_2$O) δ 140.41, 130.29, 129.99, 128.19, 41.36, 32.89, 19.40, 12.97; $^{31}$P NMR (244 MHz, D$_2$O) δ 57.25; HRMS m/z 228.0617 [M−Li]$^+$; calcd for C$_{10}$H$_{15}$NOPS 228.0617.

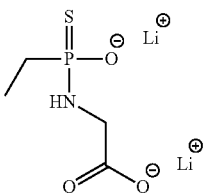

JK-9

JK-9 was prepared from 5-9 using the same procedure as for JK-1. $^1$H NMR (600 MHz, D$_2$O) δ 3.31 (m, 2H), 1.67 (m, 2H), 0.93 (m, 3H); $^{13}$C NMR (150 MHz, D$_2$O) δ 179.08, 44.86, 29.36, 7.24; $^{31}$P NMR (244 MHz, D$_2$O) δ 72.06;

Measurements of H$_2$S Release

Figure 1B:
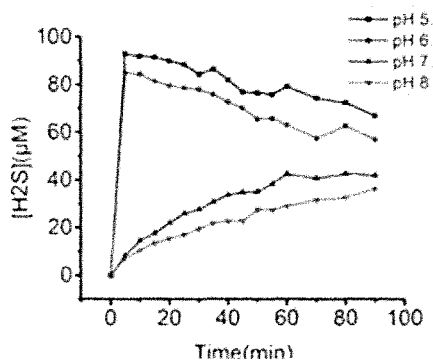
FIG. 1B. Shows $H_2S$ release profile of JK-3 under different pH.
Figure 1C:
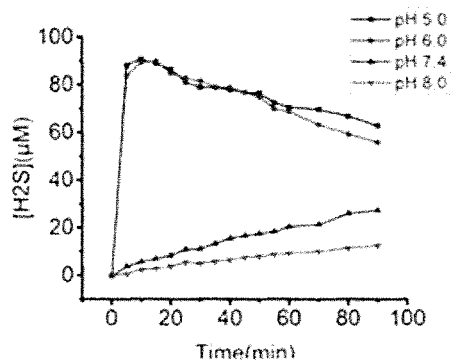
FIG. 1C. Shows $H_2S$ release profile of JK-4 under different pH.

The measurement of H2S releasing ability in aqueous buffers was initially conducted as a point of comparison to a known standard GYY4137 ((p-methoxyphenyl)morpholino-phosphinodithioic acid). It should be noted that previous measurements of H$_2$S production from GYY4137 or similar donors were mainly done by using the standard methylene blue (MB) method. However, strong acidic conditions are involved in this assay. It is known that acids can dramatically facilitate hydrolysis of phosphorothioates. Therefore, the standard MB method is not appropriate for evaluating phosphorothioate-based donors. In this disclosure, a modified zinc-sulfide precipitation based MB method13 was used. This method avoids the false signals caused by acid-promoted hydrolysis. Using this method, we found that H$_2$S releases from the JK donors were significantly affected by pH. In general, weak acidic pH (5 and 6) caused faster and more H$_2$S release while neutral and weak basic pH (7.4 and 8) caused slower and less H$_2$S release. Taking JK-1 and JK-2 as examples, their time-dependent H$_2$S release curves under different pH were compared with GYY4137 (FIG. 1). Clearly GYY4137 released very little H$_2$S under these conditions. In contrast JK-1 and JK-2 showed much-enhanced H$_2$S releasing ability. Most interestingly, JK-1 was found to be a donor that only released H$_2$S under weak acidic pH (5 and 6). It released barely detectable H$_2$S under pH 7.4 and 8. JK-2, however, showed slow and sustained H$_2$S release under pH 7.4 and 8, but much faster release under pH 5 and 6. The enhanced H$_2$S production from JK-2 is likely due to the introduction of benzyl group at the α-position, which facilitates the intramolecular cyclization. The other two donors, JK-3 and JK-4, showed similar activity like JK-2. JK-5, on the other hand, was found not to release H$_2$S at all.

H$_2$S generation from the donor was initiated by adding 100 μL of freshly prepared donor stock solution (30 mM in DI water) into 30 mL of PBS buffer (pH 5.0, 6.0, 7.4, 8.0, 50 mM). Then 1.0 mL of the solution aliquots were periodically taken and transferred to 1.5 mL EPPENDORF tubes containing 100 μL of zinc acetate (1% w/v) and 12.5 μL of NaOH solution (1.5M). This was followed by centrifugation at 20500 rcf for 20 min to pellet the zinc sulfide that had been formed. The supernatant was then removed and the pellet reconstituted with 200 μL of N, N-dimethyl-1,4-phenylenediamine sulfate (20 mM in 7.2 M HCl) and 200 μL of ferric chloride (30 mM in 1.2 M HCl). The methylene blue reaction was carried out for 15 min and the reaction was transferred to UV cuvettes containing 1 mL PBS buffer (pH 7.4, 50 mM). The absorbance (670 nm) of the resultant solution was determined. H$_2$S concentration of each sample was calculated against a calibration curve obtained by a series of Na$_2$S solutions.

Figure 2A:
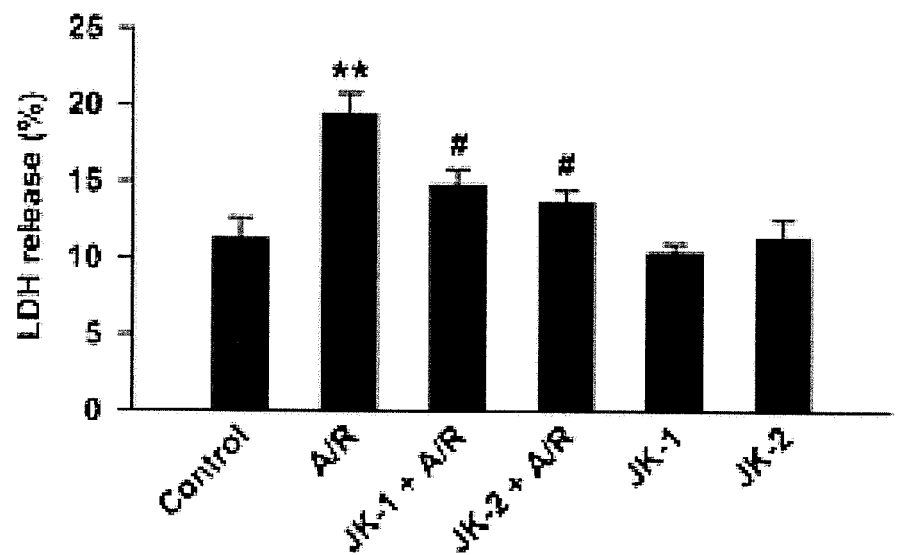
FIG. 2A. Shows the effects of JK-1 and JK-2 on A/R-induced LDH release. During anoxia 25 μM of JK-1 or JK-2 was added into medium and incubated for 1 h, respectively, and then the cells underwent a reoxygenation process. After the treatments, LDH in cells and medium was measured. Data were expressed as the mean±SEM. **$P<0.01$ vs the control group. #$P<0.05$ vs A/R alone group.
Figure 2B:
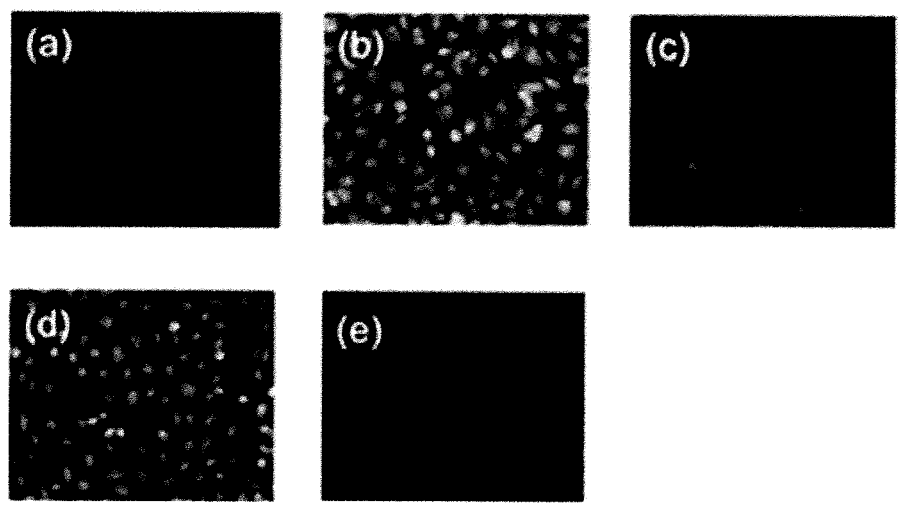
FIG. 2B. Shows the $H_2S$ production from JK-1, JK-2 and GYY4137 in HeLa cells. Cells were incubated with WSP-5 for 30 min. After removal of excess WSP-5, cells were treated with vehicle (a), $Na_2S$ (200 μM) (b), JK-1 (200 μM) (c), JK-2 (200 μM) (d), and GYY4137 (200 μM) (e). Images were taken after one hour.

The above results demonstrated that the compounds of the invention release $H_2S$ in a controlled buffer. The compounds are also capable of delivering $H_2S$ to biological systems like live cells. To this end, the compounds cytotoxicity was examined. Under our conditions, the donors (up to 400 μM) showed no cytotoxicity to H9c2 and HeLa cells. Next we validated the donors' $H_2S$ production in cells. As shown in FIG. 2, HeLa cells were first incubated with a selective $H_2S$ fluorescent probe, WSP-5, for 30 min. After the removal of extracellular probe, cells were treated with the donors (JK-1, JK-2, GYY4137, and $Na_2S$) for 1h. As expected, JK-2-treated cells exhibited strong fluorescence, which were comparable with $Na_2S$ treated cells. JK-1 and GYY4137-treated cells showed much weaker fluorescence, which was consistent with their decreased $H_2S$ release ability under neutral pH.

HeLa and H9c2 cells were cultured in Dulbecco's modified Eagle's medium (DMEM) high glucose medium supplemented with 10% fetal bovine serum (FBS) at 37° C. under a condition of 5% $CO_2$ atmosphere.

The cell counting kit (CCK)-8 was applied to measure the cell viability of HeLa cells cultured in 96-well plates. After the indicated cell treatment, 100 μL of CCK-8 solution at 1:10 dilution was added to each well and cells were incubated for a further 3 h at 37° C. Absorbance was measured at 450 nm with a microplate reader. The mean optical density (OD) of 4 wells in each group was used to calculate cell viability as follows: (experiments were performed in triplicate)

Cells were incubated with the donor at varied concentrations (100-400 μM) for 1 h and then washed by PBS buffer. CCK-8 assay was applied to measure cell viability as described above.

The effect of $H_2S$ as a cardioprotective agent against myocardial ischemia reperfusion (MI/R) injury is known in the art. The mechanisms include reducing oxidative stress, preserving mitochondrial function, decreasing myocardial inflammation, and improving angiogenesis. Given the above information the compounds of this disclosure would exhibit similar cardioprotective activities due to $H_2S$ release. To establish the cellular model of MI/R injury, H9c2 cardiomyoblasts were exposed to anoxia/reoxygenation (A/R) treatment, together with increasing concentrations of $H_2O_2$ (100-400 μM). This treatment led to a dose-dependent inhibition in cell viability, indicating that it could imitate in vivo I/R-triggered effects. Since the median lethal concentration of $H_2O_2$ in H9c2 cells was approximately 400 μM, this concentration was used for our studies.

HeLa cells were inoculated in a 24-well plate and cultured overnight. The cells were co-incubated with WSP-5 (50 μM) in PBS at 37° C. for 30 min and washed by PBS to remove extracellular WSP-5. Cells were then co-incubated with 200 μM of the donor at 37° C. for 30 min. Cell imaging was carried out after washing the cells three times with PBS (pH 7.4). All of the microscopy images were taken on a fluorescence microscope with excitation at 490 nm.

The protective effects of the disclosed compounds against A/R-induced cellular damage was examined. In these experiments, H9c2 cells were pretreated with JK-1 or JK-2 at various concentrations (12, 25 and 50 μM) for 1 h during anoxia. Cells then underwent a reoxygenation process, after which cell viability was analyzed. Results showed that JK-1 and JK-2 exhibited significant attenuation of A/R induced damage.

Figure 3A:
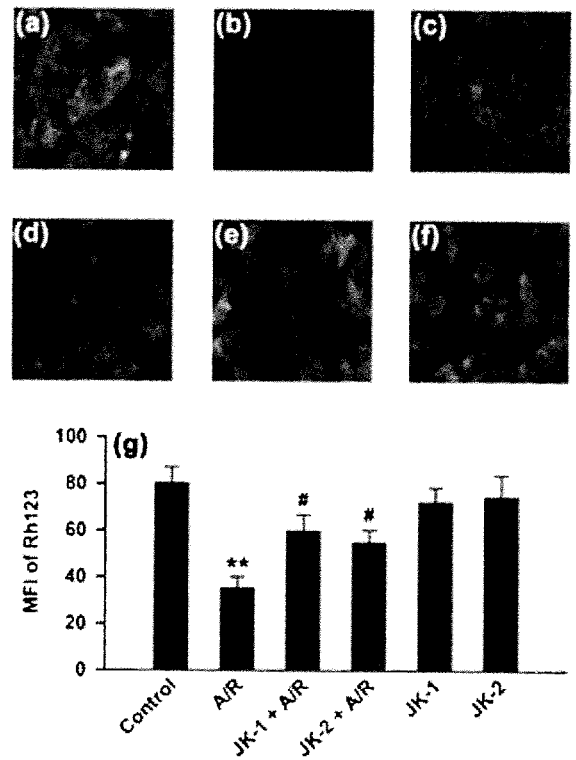
FIG. 3A. Shows the effects of JK-1 and JK-2 on A/R-induced MMP loss in H9c2 cells. (a-f) Rh123 staining followed by photofluorography to observe MMP in H9c2 cells. (a) Control group. (b) A/R alone group. During anoxia 25 μM of JK-1 (c) or JK-2 (d) was added into medium and incubated for 1 h, respectively, and then the cells underwent a reoxygenation process. The cells were pre-treated with 25 μM of JK-1 (e) or JK-2 (f) for 1 h followed by a 6 h-culture. Data were expressed as the mean±SEM. **$P<0.01$ vs the control group. #$P<0.01$ vs A/R alone group.
Figure 3B:
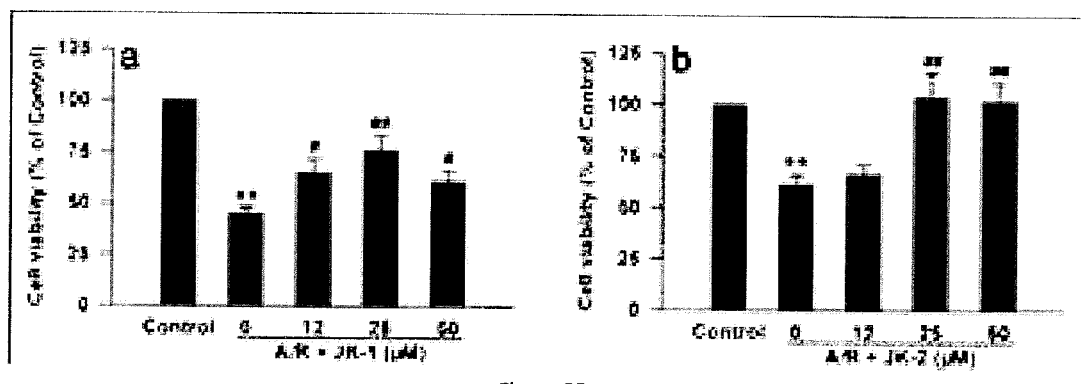
FIG. 3B. Shows the effects of JK-1 and JK-2 on A/R-induced cellular injury. During anoxia various concentrations of JK-1 and JK-2 were added into medium and incubated for 1 h, respectively. Then the cells underwent a reoxygenation process. After the treatments, the CCK-8 assay was performed to detect cell viability. Data was expressed as the mean±SEM. **$P<0.01$ vs the control group, #$P<0.05$, ##$P<0.01$ vs A/R alone group.

In addition to the cell viability assay, other methods were also used to validate JK's protective effects in cells. Lactate dehydrogenase (LDH) is a cytoplasmic protein whose leakage from the cells indicates cell damage. Preconditioning of H9c2 cells with A/R treatment remarkably enhanced LDH release, indicating that A/R treatment induced severe damage to cells. However, LDH release was significantly reduced when cells were pretreated with 25 μM JKs. In another experiment, mitochondrial membrane potential (MMP) was measured by Rh123 staining to test cellular damage. FIG. 3 shows that under normal conditions H9c2 cells had bright green fluorescence. When cells were exposed to A/R treatment, a dramatic MMP loss was observed, evidenced by weak green fluorescence. However, incubating with 25 μM JKs greatly impeded this MMP loss by preserving mitochondria functions. These results further confirmed that JKs exhibited potent cellular protection against oxidative injury.

The rate of LDH release was determined with a commercial LDH kit supplied by Thermo Fisher Scientific Inc. (Pittsburgh Pa., US). Briefly, H9c2 cells were inoculated in a 96-well plate and grew to about 70% confluence. After the indicated treatments, 50 μL of supernatant per well was carefully removed and transferred into corresponding wells for the determination of extracellular LDH levels. Then, 100 μL of DMEM with 2% Triton X-100 was added to the adherent cells to lyse the cells. Fifty microliters of cell lysate was transferred to a 96-well plate to determine intracellular LDH levels. The same volume of prepared reaction mixture was added to the supernatant or homogenate, separately, and reacted for 10 min at room temperature by gentle shaking. Stopping solution was added to stop the reaction. Absorbance was measured at 490 and 600 nm with a microplate reader.

Mitochondrial membrane potential (MMP) was observed using a fluorescent dye, rhodamine 123 (Rh123), a cell-permeable cationic dye that preferentially enters the mitochondria based on the highly negative MMP. Depolarization of MMP usually leads to a decreased intake of Rh123 and an intracellular weak fluorescence. After the indicated treatments, 10 mg/L Rh123 was added to cell cultures for 15 min at 37° C., and fluorescence was measured over the entire field of vision using a fluorescent microscope (Advanced Microscopy Group, Seattle, US). The mean fluorescent intensity (MFI) of Rh123 from four random fields was analyzed using IMAGEJ 1.41 software.

Figure 4:
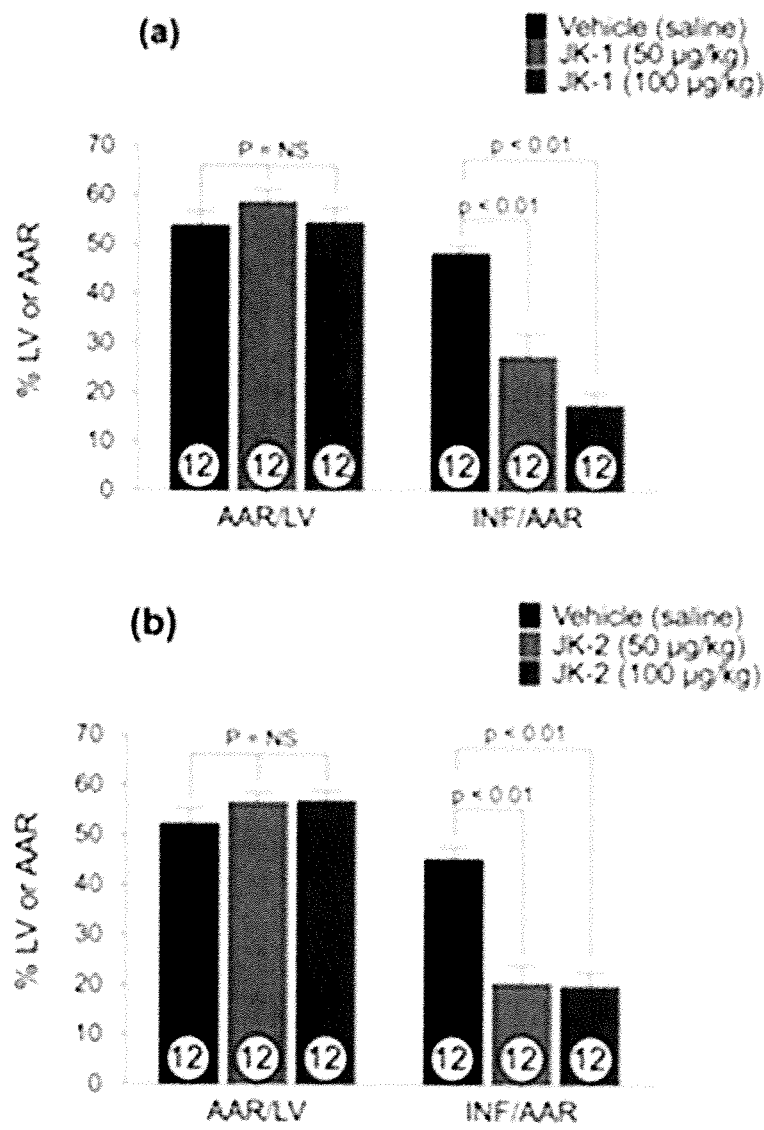
FIG. 4. Shows the cardio protective effects of JK-1 and JK-2 in myocardial ischemia-reperfusion injury. (a) Myocardial infarct size was significantly reduced in mice treated with 50 μg/kg or 100 μg/kg of JK-1 ($p<0.01$) compared to vehicle treated mice. (b) Myocardial infarct size were significantly reduced in mice treated with 50 μg/kg or 100 μg/kg of JK-2 ($p<0.01$) compared to vehicle treated mice. Results are presented as mean+/−SEM for n=12 in each group.

The reduced local pH level caused by ischemic injury was also considered, compounds where tested for their effects of representative donors, JK-1 and JK-2, against myocardial ischemia/reperfusion (MI/R) injury in a murine model. In these experiments, mice were subjected to 45 min of left ventricular ischemia followed by 24 h reperfusion. The donors or vehicle were administered by intracardiac (i.c.) injection at the time of reperfusion at different doses. All animal groups displayed similar area-at-risk per left ventricle (AAR/LV), suggesting that surgical procedure produced the same degree of ischemic damage. However, compared to vehicle treated mice, those receiving the donors displayed significant reduction in infarct size per area-at-risk (INF/AAR), assessed by 2,3,5-triphenyltetrazolium chloride (TTC) staining (FIG. 4). A 50 μg/kg and 100 μg/kg bolus of JK-1 maximally reduced INF/AAR by 43% and 64%, respectively. Similarly, 50 μg/kg and 100 μg/kg of JK-2 reduced INF/AAR by 55% and 56%, respectively.

Figure 5:
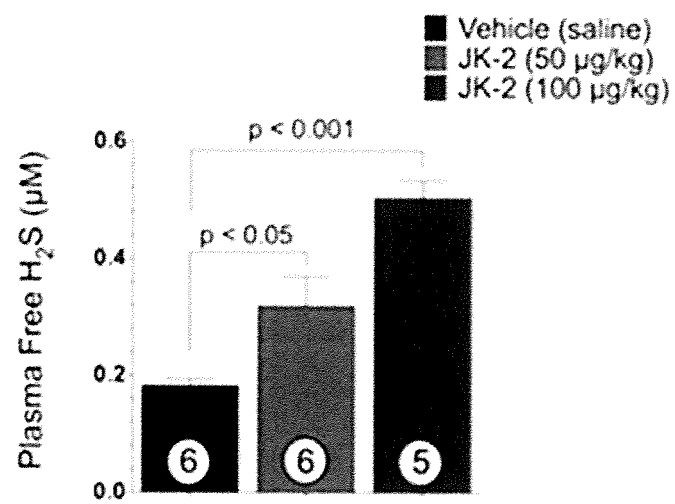
FIG. 5. Shows circulating free $H_2S$ level. Blood was collected 15 minutes after the administration of JK-2. Circulating free $H_2S$ levels were measured from plasma samples using gas chromatography and chemiluminesence methods. Free $H_2S$ level was significantly higher with 50 μg/kg or 100 μg/kg of JK-2 treatment ($p<0.05$ and $p<0.001$, respectively).
Figure 6:
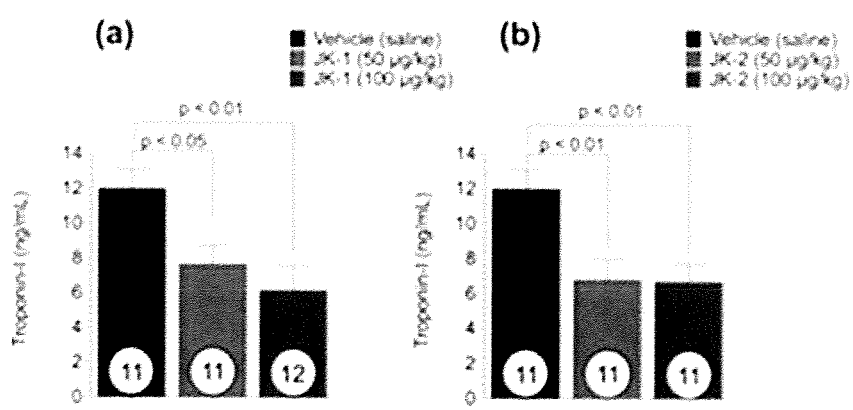
FIG. 6. Shows circulating Troponin I level. Blood was collected at 4 hours of reperfusion, and circulating cardiac troponin I levels were measured. Troponin I level was significantly reduced with either (a) 50 μg/kg or 100 μg/kg of JK-1 ($p<0.05$ and $p<0.01$, respectively) or (b) 50 μg/kg or 100 μg/kg of JK-2 treatment ($p<0.05$ and $p<0.01$, respectively).

Moreover, circulating cardiac troponin 1 levels, the marker for acute myocardial infarction, were significantly lowered with JK-1 or JK-2 treated animals ($p<0.05$ for 50 μg/kg and $p<0.01$ for 100 μg/kg in both groups). We also validated H$_2$S production from the donors. As shown in FIG. 5 the administration of JK-2 led to significant increase of free H$_2$S in blood.

Male C57BL/6J mice, 10-12 weeks of age (Jackson Laboratories, Bar Harbor, Me.) were used in the present study. All animals were housed in a temperature-controlled animal facility with a 12-h light/dark cycle, with water and rodent chow provided ad libitum. All animals received humane care in compliance with the Principles of Laboratory Animal Care formulated by the National Society of Medical Research and the Guide for the Care and Use of Laboratory Animals published by the National Institutes of Health.

Surgical occlusion of the left coronary artery (LCA), infarct size determination, and troponin I (TnI) measurements were performed as previously described. [1]C57BL6/J male mice (10-12 weeks of age) were anesthetized using pentobarbital (50 mg/kg) and ketamine (60 mg/kg) and maintained under anesthesia throughout the procedure with additional administration of pentobarbital (50 mg/kg). Mice were intubated and mechanically ventilated using a Hugo Sachs type 845 minivent. A hair removal compound was used to remove the hair on the chest of mice. The area was then cleaned using betadine and alcohol wipes alternating 3 times. The chest was opened with via a median sternotomy and the exposed ribs, muscle, and tissues were cauterized to prevent bleeding. The LCA was visualized using a dissection microscope with a fiber optic light ring, and using a 7-0 silk suture, a 3-5 mm piece of PE-10 tubing was secured over the LCA, occluding the artery. Mice were subjected to 45 min of myocardial ischemia followed by reperfusion. At the time of reperfusion, an injection of vehicle (saline), JK-1 (50 µg/kg and 100 µg/kg), or JK-2 (50 µg/kg and 100 µg/kg) was given i.c. The chest was closed in layers, closing the muscle layer first, then the skin. Mice were removed from ventilation once pedal reflex returned and it was determined that respiration was spontaneous. Mice were placed in a recovery cage and supplied with 100% O$_2$ via a nose cone. Reperfusion was allowed for 24 h, and blood samples for TnI measurements were taken at 4 h after time of reperfusion. At 24 h of reperfusion, the LV area at risk (AAR) and infarct size were determined by Evans blue and 2,3,5-tetrazolium chloride staining.

On the day of experimentation, test compounds were dissolved in 0.2 mL of sterile saline. For in vivo experiments, the test compounds were further diluted in sterile saline to final concentrations of 0.05 or 0.1 mg/mL. Then, various volumes were administered based on the animals' weights to obtain the correct dosage.

Blood samples were collected via a tail vein at 4 h of reperfusion. Cardiac troponin I level was measured in serum using the Life Diagnostic high sensitivity mouse cardiac troponin I ELISA kit following the manufacturer's instructions.

FIGS. 7-10 summarize additional experimental results with the new compounds and demonstrate their particular utility in addressing heart failure.

Figure 7:
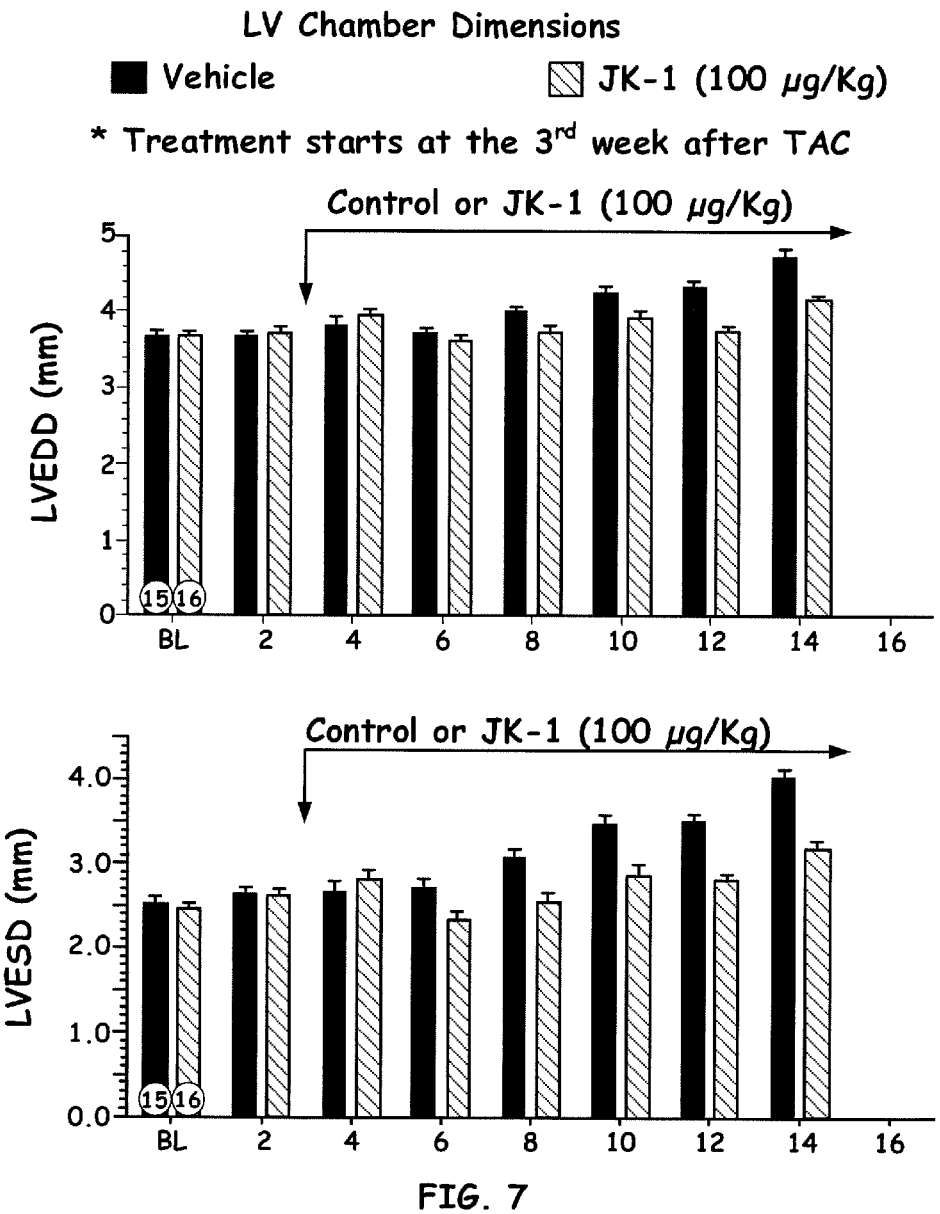
FIGS. 7-10. Are bar graphs illustrating particular utility of the inventive compounds in addressing heart failure.

FIG. 7. Left ventricular dimensions at end-diastole (LVEDD) and at end-systole in millimeters (mm) at baseline and following heart failure in C57BL6/J mice. Mice were subjected to transverse aortic constriction (TAC) surgery to induce pressure overload hypertrophy and heart failure with reduced ejection fraction. LVEDD and LVESD were measured using high-resolution echocardiography at baseline and every 2 weeks thereafter for a period of 14 weeks. The H2S donor, (JK1) was administered starting at 3 weeks post-TAC at a dose of 100 µg/kg administered once daily via intraperitoneal injection. Administration of JK1 significantly reduced left ventricular dilatation. Following heart failure the heart dilates and this adverse remodeling response contributes to reduced cardiac function. JK1 attenuated this adverse remodeling response and these data demonstrate cardioprotective actions of JK1 in heart failure.

Figure 8:
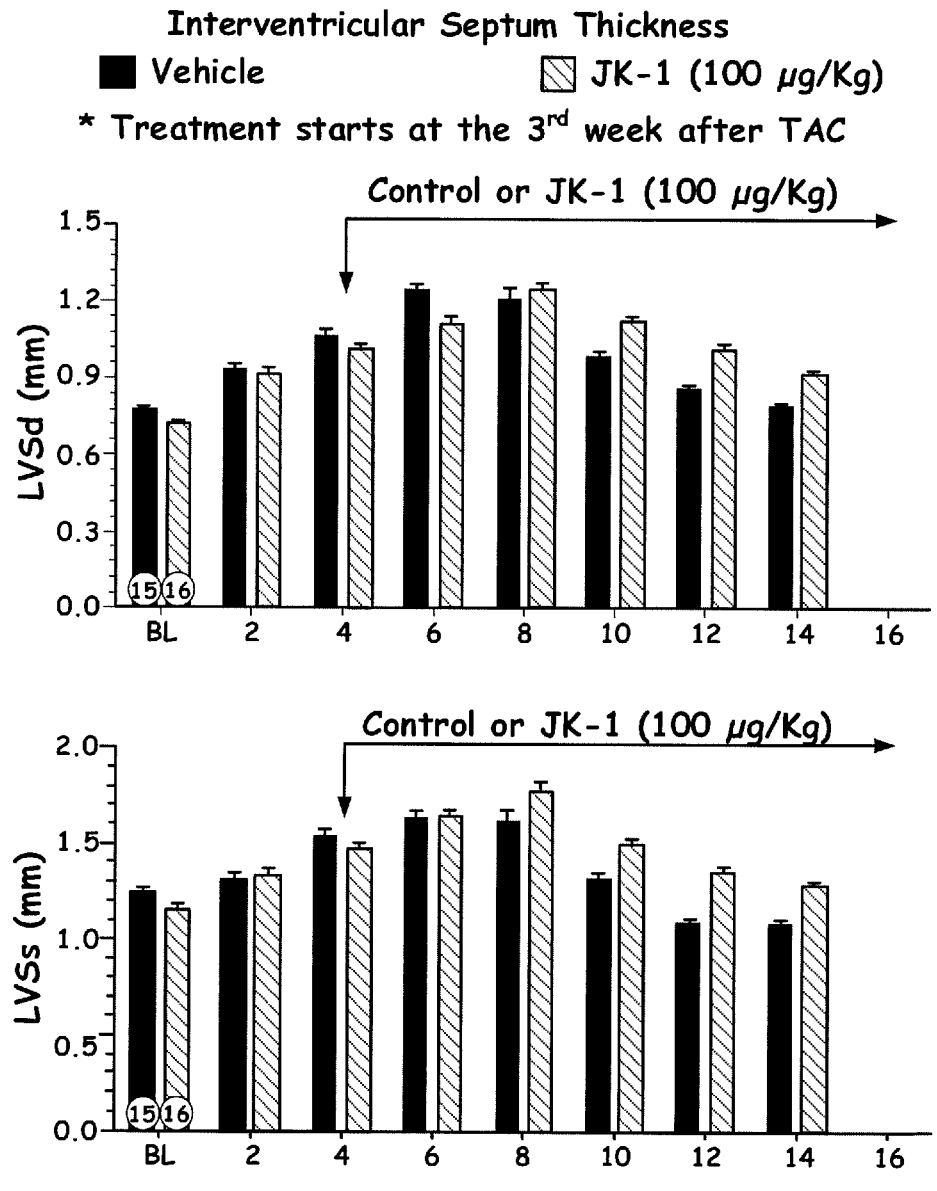

FIG. 8. Interventricular septum thickness measured at end-diastole (IVSd) and at end-systole (IVSs) in millimeters (mm) at baseline and following heart failure in C57BL6/J mice. Mice were subjected to transverse aortic constriction (TAC) surgery to induce pressure overload hypertrophy and heart failure with reduced ejection fraction. IVSd and IVSs were measured using high-resolution echocardiography at baseline and every 2 weeks thereafter for a period of 14 weeks. The H2S donor, (JK1) was administered starting at 3 weeks post-TAC at a dose of 100 µg/kg administered once daily via intraperitoneal injection. Administration of JK1 significantly preserved IVSd and IVSs and attenuated myocardial septal wall thinning in the setting of TAC-induced heart failure. Myocardial wall thinning is a significant pathological component of heart failure. These data provide evidence that JK1 protects the failing heart.

Figure 9:
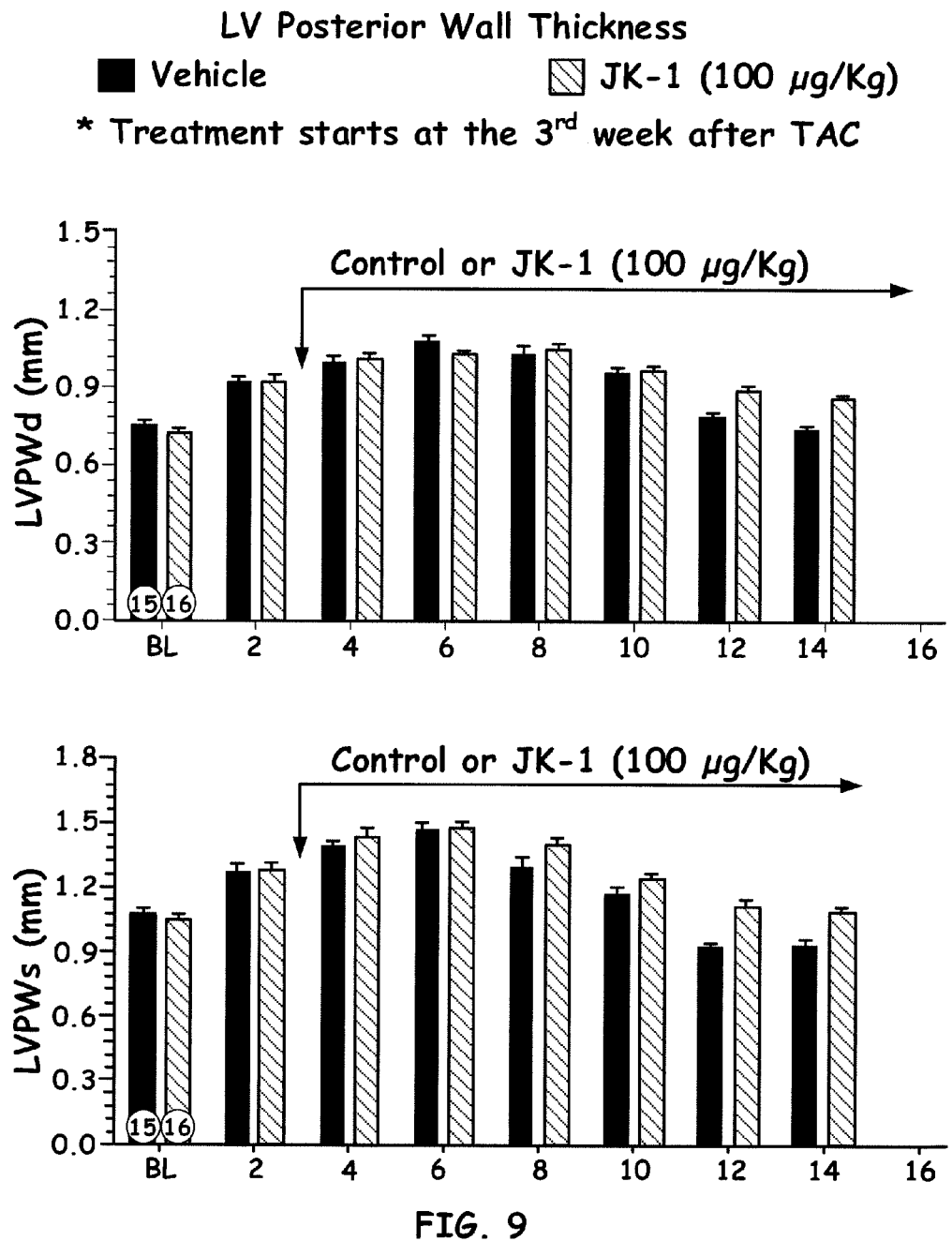

FIG. 9. Left ventricular (LV) posterior wall thickness (PW) measured at end-diastole (d) and and at end-systole (s) in millimeters (mm) at baseline and following heart failure in C57BL6/J mice. Mice were subjected to transverse aortic constriction (TAC) surgery to induce pressure overload hypertrophy and heart failure with reduced ejection fraction LVPWd and LVPWs were measured using high-resolution echocardiography at baseline and every 2 weeks thereafter for a period of 14 weeks. The H2S donor, (JK1) was administered starting at 3 weeks post-TAC at a dose of 100 µg/kg administered once daily via intraperitoneal injection. Administration of JK1 significantly preserved left ventricular wall thickness. These data suggest that JK1 exerts beneficial effects in terms of cardiac remodeling in heart failure.

Figure 10:
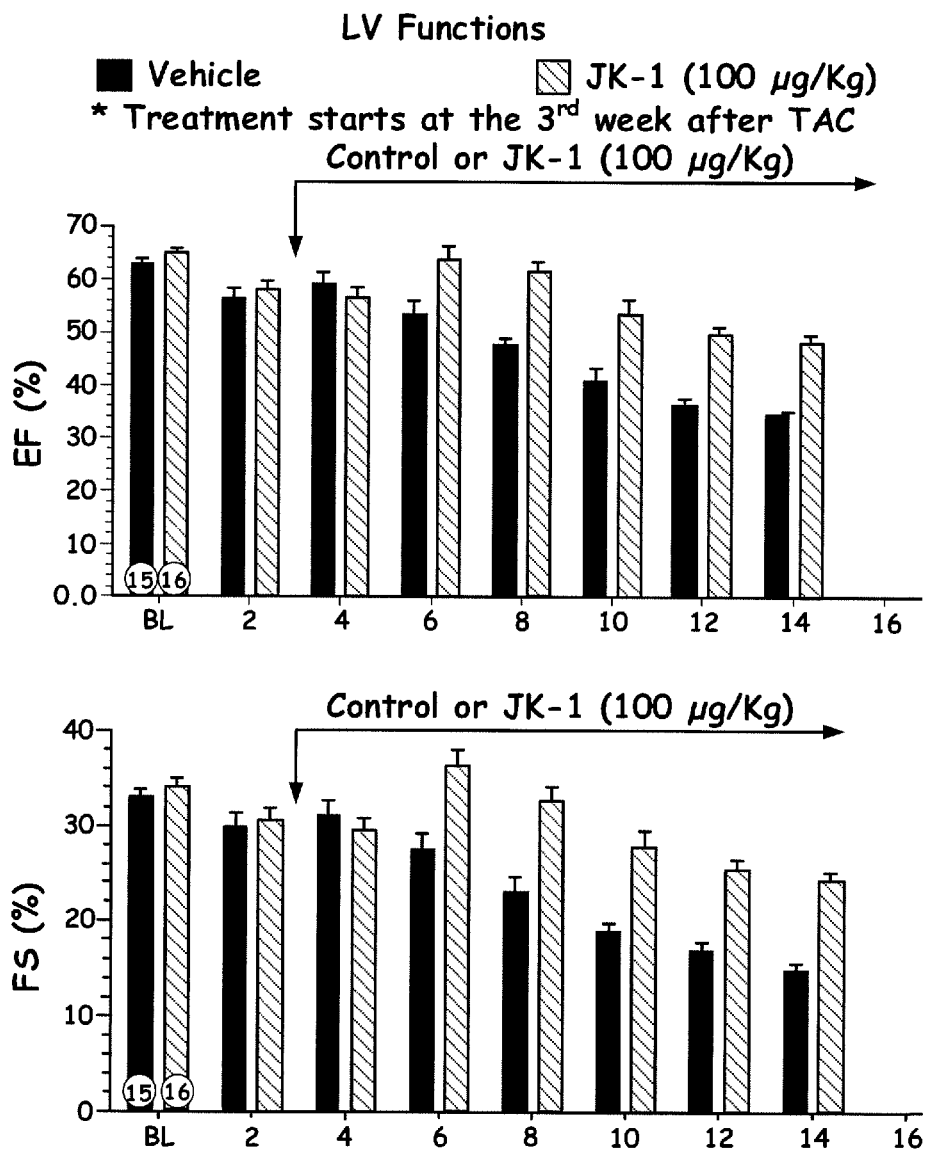

FIG. 10. Left ventricular (LV) ejection fraction (EF) and fractional shortening (FS) at baseline and following heart failure in C57BL6/J mice. Mice were subjected to transverse aortic constriction (TAC) surgery to induce pressure overload hypertrophy and heart failure with reduced ejection fraction. LVEF (%) and LVFS (%) were measured using high-resolution echocardiography at baseline and every 2 weeks thereafter for a period of 14 weeks. The H2S donor, (JK1) was administered starting at 3 weeks post-TAC at a dose of 100 µg/kg administered once daily via intraperitoneal injection. LVEF and LVFS are clinically utilized measures of cardiac function. In heart failure both LVEF and LVFS are significantly reduced and contribute to morbidity and mortality in patients that suffer from heart failure. Administration of JK1 significantly preserved both LVEF and LVFS further demonstrating the protective actions of this novel H$_2$S donor.

It should be emphasized that the above-described embodiments are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

We claim:
1. A compound having the formula

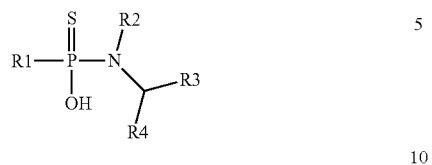

wherein
R1 is aryl, alkyl, aralkyl, and substituted aryl or a combination thereof;
R2 is a hydrogen, or a part of a 3 to 7 membered ring system connecting R2 to R3;
R3 is a hydrogen, or part of the 3 to 7 membered ring system connecting to R2 to R3,
wherein the 3 to 7 membered ring system connecting R2 to R3, when present, is an optionally substituted, fully saturated or unsaturated, aromatic or a nonaromatic cyclic or hetrocyclic group;
R4 is an alkyl or a carboxylic acid,
or a pharmaceutically acceptable salt thereof, a tautomer thereof, or a pharmaceutically acceptable salt of the tautomer.

2. A compound of claim 1, wherein R1 is phenyl, R2 and R3 is a heterocycle which is a 4 membered ring system, and R4 is a carboxylic acid.

* * * * *